US007725973B2

(12) United States Patent  (10) Patent No.: US 7,725,973 B2
Blaustein et al.  (45) Date of Patent: *Jun. 1, 2010

(54) ELECTRIC TOOTHBRUSHES

(75) Inventors: Lawrence A. Blaustein, Moreland Hills, OH (US); Douglas A. Gall, Strongsville, OH (US); Patrick W. Brown, Auburn, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/893,469

(22) Filed: Aug. 16, 2007

(65) Prior Publication Data

US 2008/0016633 A1  Jan. 24, 2008

Related U.S. Application Data

(63) Continuation of application No. 11/486,725, filed on Jul. 14, 2006, now Pat. No. 7,640,615, which is a continuation of application No. 10/308,959, filed on Dec. 3, 2002, now abandoned.

(60) Provisional application No. 60/361,625, filed on Mar. 4, 2002.

(51) Int. Cl.
A61C 17/22 (2006.01)
A61C 17/34 (2006.01)

(52) U.S. Cl. .......................... 15/22.2; 15/22.1
(58) Field of Classification Search ............ 15/22.1, 15/22.2, 22.4, 28
See application file for complete search history.

(56) References Cited

U.S. PATENT DOCUMENTS 793,587 A 6/1905 Johnson
1,110,406 A 9/1914 Schreck
1,212,001 A 1/1917 Baxter
1,255,028 A 1/1918 Leonard et al.
1,392,623 A 10/1921 Cheatham (Continued)

FOREIGN PATENT DOCUMENTS

CH 358408 1/1962

(Continued)

OTHER PUBLICATIONS

Bader, "Review of Currently Available Battery-Operated Toothbrushes", *Compend. Contin. Educ. Dent.*, vol. 13, No. 12, p. 1162, 1164-1169.

(Continued)

*Primary Examiner*—Mark Spisich
(74) *Attorney, Agent, or Firm*—Vladimir Vitenberg; George H. Leal

(57) ABSTRACT

An electric toothbrush is provided. The electric toothbrush includes a handle having an electric motor, a head, and a neck extending between the handle and the head. The head has first end disposed adjacent to the neck and a second end opposite the first end. The head has a first bristle holder with a plurality of bristles disposed therein and a second bristle holder having a plurality of bristles disposed therein. The first bristle holder is located at the second end of said head. A rotating shaft is operatively connected to the electric motor and to the first moving bristle holder to reciprocate the first moving bristle holder in a direction transverse to a longitudinal axis of the head.

8 Claims, 8 Drawing Sheets

U.S. PATENT DOCUMENTS

| | | | |
|---|---|---|---|
| 1,517,320 A | 12/1924 | Stoddart | |
| 1,553,456 A * | 9/1925 | Metrakos | 15/52.2 |
| 1,557,244 A | 10/1925 | Dominque | |
| 1,896,731 A | 2/1933 | Lippett | |
| 1,981,688 A | 11/1934 | Conti | |
| 1,997,352 A | 4/1935 | Fleet | |
| 2,044,863 A | 6/1936 | Sticht | |
| 2,140,307 A | 12/1938 | Belaschk et al. | |
| 2,172,624 A | 9/1939 | Robert | |
| 2,215,031 A | 9/1940 | Elmore | |
| 2,267,916 A | 12/1941 | Hershey | |
| 2,379,049 A | 6/1945 | Tompkins | |
| 2,435,421 A | 2/1948 | Blair | |
| 2,601,567 A | 6/1952 | Steinberg | |
| 3,115,652 A | 12/1963 | Zerbee | |
| 3,129,449 A | 4/1964 | Cyzer | |
| 3,159,859 A | 12/1964 | Rasmussen | |
| 3,160,902 A | 12/1964 | Aymar | |
| 3,178,754 A | 4/1965 | Cleverdon | |
| 3,195,537 A | 7/1965 | Blasi | |
| 3,242,516 A | 3/1966 | Cantor | |
| 3,350,737 A | 11/1967 | Makowsky | |
| 3,379,906 A | 4/1968 | Spohr | |
| 3,398,421 A | 8/1968 | Rashbaum | |
| 3,509,874 A | 5/1970 | Stillman | |
| 3,524,088 A | 8/1970 | Ryckman | |
| 3,538,530 A | 11/1970 | Stemme | |
| 3,588,936 A | 6/1971 | Duve | |
| 3,592,188 A | 7/1971 | Barnett | |
| 3,935,869 A | 2/1976 | Reinsch | |
| 3,945,076 A | 3/1976 | Sung | |
| 3,978,852 A | 9/1976 | Annoni | |
| 4,027,348 A | 6/1977 | Flowers et al. | |
| 4,156,620 A | 5/1979 | Clemens | |
| 4,175,299 A | 11/1979 | Teague, Jr. et al. | |
| 4,274,173 A | 6/1981 | Cohen | |
| 4,326,314 A | 4/1982 | Moret et al. | |
| 4,346,492 A | 8/1982 | Solow | |
| 4,397,055 A | 8/1983 | Cuchiara | |
| 4,545,087 A | 10/1985 | Nahum | |
| 4,654,922 A | 4/1987 | Chen | |
| 4,791,945 A | 12/1988 | Moriyama | |
| 4,795,347 A | 1/1989 | Maurer | |
| 4,845,795 A | 7/1989 | Crawford | |
| 4,974,278 A | 12/1990 | Hommann | |
| 4,989,287 A | 2/1991 | Scherer | |
| 4,995,131 A | 2/1991 | Takeda | |
| 5,033,150 A | 7/1991 | Gross et al. | |
| 5,068,939 A | 12/1991 | Holland | |
| 5,070,567 A | 12/1991 | Holland | |
| 5,077,855 A | 1/1992 | Ambasz | |
| 5,088,145 A | 2/1992 | Whitefield | |
| 5,114,214 A | 5/1992 | Barman | |
| 5,120,225 A | 6/1992 | Amit | |
| 5,137,039 A | 8/1992 | Klinkhammer | |
| 5,138,734 A | 8/1992 | Chung | |
| 5,170,525 A | 12/1992 | Cafaro | |
| 5,186,627 A | 2/1993 | Amit et al. | |
| 5,224,764 A | 7/1993 | Klinkhammer | |
| 5,226,206 A | 7/1993 | Davidovitz et al. | |
| 5,228,466 A | 7/1993 | Klinkhammer | |
| 5,253,382 A | 10/1993 | Beny | |
| 5,259,083 A * | 11/1993 | Stansbury, Jr. | 15/22.1 |
| 5,276,932 A | 1/1994 | Byrd | |
| 5,301,381 A | 4/1994 | Klupt | |
| 5,305,492 A | 4/1994 | Giuliani et al. | |
| 5,311,633 A | 5/1994 | Herzog et al. | |
| 5,321,866 A | 6/1994 | Klupt | |
| 5,353,460 A | 10/1994 | Bauman | |
| 5,359,747 A | 11/1994 | Amakasu | |
| 5,378,153 A | 1/1995 | Giuliani et al. | |
| 5,383,242 A | 1/1995 | Bigler et al. | |
| 5,398,366 A | 3/1995 | Bradley | |
| 5,404,608 A | 4/1995 | Hommann | |
| 5,416,942 A | 5/1995 | Baldacci et al. | |
| 5,448,792 A | 9/1995 | Wiedemann et al. | |
| 5,465,444 A | 11/1995 | Bigler et al. | |
| 5,493,747 A | 2/1996 | Inakagata et al. | |
| 5,504,958 A | 4/1996 | Herzog | |
| 5,504,959 A | 4/1996 | Yukawa et al. | |
| 5,524,312 A * | 6/1996 | Tan et al. | 15/22.1 |
| 5,528,786 A | 6/1996 | Porat et al. | |
| 5,577,285 A | 11/1996 | Drossler | |
| 5,617,601 A | 4/1997 | McDougall | |
| 5,617,603 A | 4/1997 | Mei | |
| 5,625,916 A | 5/1997 | McDougall | |
| 5,679,991 A | 10/1997 | Wolf | |
| 5,687,442 A | 11/1997 | McLain | |
| 5,727,273 A | 3/1998 | Pai | |
| 5,732,432 A | 3/1998 | Hui | |
| 5,732,433 A | 3/1998 | Droessler et al. | |
| 5,738,575 A | 4/1998 | Bock | |
| 5,778,474 A * | 7/1998 | Shek | 15/22.1 |
| 5,784,743 A | 7/1998 | Shek | |
| 5,813,079 A | 9/1998 | Halm | |
| RE35,941 E | 11/1998 | Stansbury, Jr. | |
| 5,836,030 A | 11/1998 | Hazeu et al. | |
| 5,842,244 A | 12/1998 | Hilfinger | |
| 5,842,245 A * | 12/1998 | Pai | 15/22.1 |
| 5,850,655 A * | 12/1998 | Gocking et al. | 15/28 |
| 5,862,558 A | 1/1999 | Hilfinger et al. | |
| 5,867,856 A | 2/1999 | Herzog | |
| 5,956,797 A | 9/1999 | Wilson | |
| 5,974,613 A | 11/1999 | Herog | |
| 5,974,615 A | 11/1999 | Schwarz-Hartmann et al. | |
| 6,000,083 A | 12/1999 | Blaustein et al. | |
| 6,106,290 A | 8/2000 | Weissman | |
| 6,138,310 A | 10/2000 | Porper et al. | |
| 6,148,462 A | 11/2000 | Zseng | |
| 6,178,579 B1 | 1/2001 | Blaustein et al. | |
| 6,189,693 B1 | 2/2001 | Blaustein et al. | |
| 6,195,828 B1 | 3/2001 | Fritsch | |
| 6,237,178 B1 | 5/2001 | Krammer et al. | |
| 6,308,359 B2 | 10/2001 | Fritsch et al. | |
| 6,311,837 B1 | 11/2001 | Blaustein et al. | |
| 6,347,425 B1 | 2/2002 | Fattori et al. | |
| 6,360,395 B2 | 3/2002 | Blaustein et al. | |
| 6,371,294 B1 | 4/2002 | Blaustein et al. | |
| D459,081 S | 6/2002 | Eliav et al. | |
| 6,421,865 B1 | 7/2002 | McDougall | |
| 6,421,866 B1 | 7/2002 | McDougall | |
| 6,434,773 B1 | 8/2002 | Kuo | |
| 6,446,294 B1 | 9/2002 | Specht | |
| 6,453,498 B1 | 9/2002 | Wu | |
| 6,463,615 B1 | 10/2002 | Gruber et al. | |
| 6,510,575 B2 | 1/2003 | Calabrese | |
| 6,536,066 B2 | 3/2003 | Dickie | |
| 6,546,585 B1 | 4/2003 | Blaustein et al. | |
| 6,564,940 B2 | 5/2003 | Blaustein et al. | |
| 6,574,820 B1 | 6/2003 | DePuydt et al. | |
| 6,626,398 B1 | 9/2003 | Cox et al. | |
| 6,725,490 B2 | 4/2004 | Blaustein et al. | |
| 6,751,823 B2 | 6/2004 | Biro et al. | |
| 6,760,946 B2 | 7/2004 | DePuydt | |
| 6,836,917 B2 | 1/2005 | Blaustein et al. | |
| 6,889,401 B2 | 5/2005 | Fattori et al. | |
| 6,892,412 B2 | 5/2005 | Gatzemeyer et al. | |
| 6,892,413 B2 | 5/2005 | Blaustein et al. | |
| 6,928,685 B1 | 8/2005 | Blaustein et al. | |
| 6,932,216 B2 | 8/2005 | Blaustein et al. | |
| 6,944,901 B2 | 9/2005 | Gatzemeyer et al. | |
| 6,952,854 B2 | 10/2005 | Blaustein et al. | |
| 6,966,093 B2 | 11/2005 | Eliav et al. | |
| 6,983,507 B2 | 1/2006 | McDougall | |

| | | |
|---|---|---|
| 7,124,461 B2 | 10/2006 | Blaustein et al. |
| 7,137,163 B2 | 11/2006 | Gatzemeyer et al. |
| 7,140,058 B2 | 11/2006 | Gatzemeyer et al. |
| 7,140,059 B2 | 11/2006 | Scherl |
| 7,150,061 B2 | 12/2006 | Kwong |
| 7,162,764 B2 | 1/2007 | Drossler et al. |
| 7,225,494 B2 | 6/2007 | Chan et al. |
| 7,258,747 B2 | 8/2007 | Vago et al. |
| 7,302,726 B2 | 12/2007 | Braun |
| 7,356,866 B2 | 4/2008 | Chan |
| 7,386,904 B2 | 6/2008 | Fattori |
| 7,392,562 B2 | 7/2008 | Boland et al. |
| 7,421,753 B2 | 9/2008 | Chan et al. |
| 7,430,777 B2 | 10/2008 | Scherl |
| 7,430,778 B2 | 10/2008 | Gatzemeyer et al. |
| 7,451,514 B2 | 11/2008 | Blaustein et al. |
| 7,520,016 B2 | 4/2009 | Kressner |
| 7,552,497 B2 | 6/2009 | Gatzemeyer et al. |
| 2002/0017474 A1 | 2/2002 | Blaustein et al. |
| 2002/0020645 A1 | 2/2002 | Blaustein et al. |
| 2002/0029988 A1 | 3/2002 | Blaustein et al. |
| 2002/0032941 A1 | 3/2002 | Blaustein et al. |
| 2002/0038772 A1 | 4/2002 | Blaustein et al. |
| 2002/0059685 A1 | 5/2002 | Paffrath |
| 2002/0078514 A1 | 6/2002 | Blaustein et al. |
| 2002/0138926 A1 | 10/2002 | Brown, Jr. |
| 2002/0152564 A1 | 10/2002 | Blaustein et al. |
| 2003/0066145 A1 | 4/2003 | Prineppi |
| 2003/0074751 A1 | 4/2003 | Wu |
| 2003/0084525 A1 | 5/2003 | Blaustein et al. |
| 2003/0084526 A1 | 5/2003 | Brown et al. |
| 2003/0084527 A1 | 5/2003 | Brown et al. |
| 2003/0140435 A1 | 7/2003 | Eliav et al. |
| 2003/0140437 A1* | 7/2003 | Eliav et al. .................. 15/22.2 |
| 2003/0154567 A1 | 8/2003 | Drossler et al. |
| 2003/0163881 A1 | 9/2003 | Driesen et al. |
| 2003/0163882 A1 | 9/2003 | Blaustein et al. |
| 2003/0182743 A1 | 10/2003 | Gatzemeyer et al. |
| 2003/0182744 A1 | 10/2003 | Fattori et al. |
| 2003/0182746 A1* | 10/2003 | Fattori et al. .................. 15/22.1 |
| 2003/0192139 A1 | 10/2003 | Fattori et al. |
| 2003/0196283 A1 | 10/2003 | Eliav et al. |
| 2003/0213075 A1 | 11/2003 | Hui et al. |
| 2003/0226223 A1 | 12/2003 | Chan et al. |
| 2004/0010869 A1 | 1/2004 | Fattori et al. |
| 2004/0025274 A1 | 2/2004 | Moskovich et al. |
| 2004/0045105 A1 | 3/2004 | Eliav et al. |
| 2004/0060137 A1 | 4/2004 | Eliav et al. |
| 2004/0074026 A1 | 4/2004 | Blaustein et al. |
| 2004/0083566 A1 | 5/2004 | Blaustein |
| 2004/0088807 A1 | 5/2004 | Blaustein et al. |
| 2004/0143917 A1 | 7/2004 | Ek |
| 2004/0168272 A1 | 9/2004 | Prineppi |
| 2004/0177458 A1 | 9/2004 | Chan et al. |
| 2004/0177462 A1 | 9/2004 | Brown, Jr. |
| 2005/0000043 A1 | 1/2005 | Chan et al. |
| 2005/0000045 A1 | 1/2005 | Blaustein |
| 2005/0091771 A1 | 5/2005 | Blaustein et al. |
| 2005/0102776 A1 | 5/2005 | Mathur |
| 2005/0155167 A1 | 7/2005 | Gall |
| 2005/0204491 A1 | 9/2005 | Gatzemeyer et al. |
| 2005/0268409 A1 | 12/2005 | Blaustein et al. |
| 2005/0278874 A1 | 12/2005 | Blaustein et al. |
| 2006/0032006 A1 | 2/2006 | Gall |
| 2006/0048314 A1 | 3/2006 | Kressner |
| 2006/0048315 A1 | 3/2006 | Chan et al. |
| 2006/0137118 A1 | 6/2006 | Blaustein |
| 2006/0254006 A1 | 11/2006 | Blaustein et al. |
| 2006/0254007 A1 | 11/2006 | Banning |
| 2007/0251033 A1 | 11/2007 | Gall |
| 2008/0010761 A1 | 1/2008 | Blaustein et al. |
| 2008/0016633 A1 | 1/2008 | Blaustein et al. |
| 2008/0078040 A1 | 4/2008 | Braun |
| 2009/0106923 A1 | 4/2009 | Boland |

FOREIGN PATENT DOCUMENTS

| | | |
|---|---|---|
| CN | 2271352 | 7/1996 |
| CN | 2236827 Y | 10/1996 |
| CN | 2271353 | 10/1996 |
| CN | 2274947 Y | 2/1998 |
| CN | 1187341 A | 7/1998 |
| CN | 2324987 | 6/1999 |
| CN | 2324988 | 6/1999 |
| CN | 2681701 Y | 3/2005 |
| DE | 3406112 | 8/1985 |
| DE | 3544256 | 8/1987 |
| DE | 4003305 | 8/1991 |
| DE | 29600236 | 4/1996 |
| DE | 29613608 | 11/1996 |
| DE | 29618755 | 3/1997 |
| DE | 19701964 | 7/1998 |
| DE | 298 09 977 | 2/1999 |
| DE | 19802904 | 7/1999 |
| DE | 19803311 | 8/1999 |
| DE | 10208529 C1 | 10/2003 |
| EP | 259648 | 3/1988 |
| EP | 0 990 424 A1 | 4/2000 |
| EP | 1053721 | 11/2000 |
| EP | 1059049 | 12/2000 |
| GB | 2247297 * | 2/1992 |
| GB | 2290224 | 12/1995 |
| GB | 2319170 | 5/1998 |
| JP | 40-8743 | 8/1965 |
| JP | 57-89810 | 6/1982 |
| JP | 2-19241 | 2/1990 |
| JP | 02-218309 | 8/1990 |
| JP | 5-146313 * | 6/1993 |
| JP | 05-146314 | 6/1993 |
| JP | 7-116020 | 5/1995 |
| JP | 7-116021 | 5/1995 |
| JP | 7-116023 | 5/1995 |
| JP | 07-116024 | 5/1995 |
| JP | 7-93892 | 10/1995 |
| JP | 8-322641 | 10/1996 |
| JP | 8-322641 * | 12/1996 |
| JP | 08-322641 A2 | 12/1996 |
| JP | 10-066704 | 3/1998 |
| JP | 10-66704 * | 3/1998 |
| JP | 2804940 | 7/1998 |
| KR | 1984-0004668 | 9/1984 |
| KR | 1986-0001137 | 6/1986 |
| KR | 1994-0013418 | 7/1994 |
| KR | 1995-0002814 | 2/1995 |
| KR | 1995-0010820 | 5/1995 |
| KR | 1997-0000408 | 1/1997 |
| KR | 1997-0000409 | 1/1997 |
| KR | 1995-0024551 | 4/1998 |
| KR | 143460 | 4/1998 |
| TW | 248031 | 12/1982 |
| TW | 233472 | 5/1983 |
| TW | 274724 | 4/1984 |
| TW | 256049 | 1/1993 |
| TW | 238504 | 6/1993 |
| TW | 253174 | 7/1994 |
| TW | 294031 | 11/1994 |
| TW | 239964 | 2/1995 |
| TW | 309753 | 7/1997 |
| TW | 330411 | 4/1998 |
| TW | 406557 | 9/2000 |
| TW | 257968 | 7/2006 |
| WO | WO 97/34545 | 9/1997 |
| WO | 99/12492 * | 3/1999 |
| WO | WO 01/06946 | 2/2001 |
| WO | WO 01/06947 | 2/2001 |
| WO | WO 01/21094 | 3/2001 |

| | | |
|---|---|---|
| WO | WO 01/43586 | 6/2001 |
| WO | WO 02/102187 A1 | 12/2002 |
| WO | WO 03/020159 | 3/2003 |
| WO | WO 03/075712 A1 | 9/2003 |
| WO | WO 2004/045448 A1 | 6/2004 |

OTHER PUBLICATIONS

U.S. Appl. No. 10/237,902, filed Sep. 9, 2002 entitled Topper for Power Toothbrush and Method for Forming the Same, all pages.
Photographs of electric toothbrush of BioBrush Industries (22 photographs).
Photos of Electric Toothbrush Head Refill.
Office Action for U.S. Appl No. 10/903,222; P&G Case 8777C; dated Apr. 11, 2005.
Office Action for U.S. Appl. No. 10/903,222; P&G Case 8777C; dated Oct. 19, 2004.
Office Action for U.S. Appl. No. 11/200,680; P&G Case 8777CC; dated Sep. 22, 2005.
Office Action for U.S. Appl. No. 11/358,582; P&G Case 8777CCC; dated Mar. 17, 2008.
Office Action for U.S. Appl. No. 11/358,582; P&G Case 8777CCC; dated Apr. 14, 2006.
Office Action for U.S. Appl. No. 11/358,582; P&G Case 8777CCC; dated Apr. 17, 2007.
Advisory Action for U.S. Appl. No. 11/358,582; P&G Case 8777CCC; dated Jun. 9, 2008.
Advisory Action for U.S. Appl. No. 11/358,582; P&G Case 8777CCC; dated Jul. 27, 2007.
Office Action for U.S. Appl. No. 11/358,582; P&G Case 8777CCC; dated Sep. 5, 2008.
Office Action for U.S. Appl. No. 11/358,582; P&G Case 8777CCC; dated Sep. 6, 2007.
Office Action for U.S. Appl. No. 11/358,582; P&G Case 8777CCC; dated Sep. 29, 2006.
Office Action for U.S. Appl. No. 10/676,955; P&G Case 8778CC; dated Jan. 24, 2005.
Office Action for U.S. Appl. No. 10/676,955; P&G Case 8778CC; dated Jan. 24, 2005.
Office Action for U.S. Appl. No. 10/676,955; P&G Case 8778CC; dated Jul. 12, 2005.
Office Action for U.S. Appl. No. 10/676,955; P&G Case 8778CC; dated Jul. 29, 2004.
Office Action for U.S. Appl. No. 10/927,845; P&G Case 8778CCC2; dated Dec. 28, 2004.
Office Action for U.S. Appl. No. 10/929,288; P&G Case 8778CCC3; dated Mar. 18, 2005.
Office Action for U.S. Appl. No. 10/929,288; P&G Case 8778CCC3; dated Aug. 24, 2005.
Office Action for U.S. Appl. No. 11/514,742; P&G Case 8778CCC3C; dated Mar. 17, 2008.
Office Action for U.S. Appl. No. 11/514,742; P&G Case 8778CCC3C; dated Aug. 17, 2007.
Office Action for U.S. Appl. No. 11/514,742; P&G Case 8778CCC3C; dated Apr. 10, 2008.
Office Action for U.S. Appl. No. 11/006,972; P&G Case 8778CCC4; dated Mar. 24, 2005.
Office Action for U.S. Appl. No. 10/896,540; P&G Case 8778CCC; dated Oct. 4, 2004.
Office Action for U.S. Appl. No. 11/414,908; P&G Case 8829RRCC; dated May 23, 2007.
Office Action for U.S. Appl. No. 11/801,000; P&G Case 8829RRCCC; dated Jun. 20, 2008.
Office Action for U.S. Appl. No. 11/801,000; P&G Case 8829RRCCC; dated Sep. 26, 2008.
Office Action for U.S. Appl. No. 11/801,000; P&G Case 8829RRCCC; dated Oct. 26, 2007.
Office Action for U.S. Appl. No. 11/801,000; P&G Case 8829RRCCC; dated Dec. 5, 2008.
Office Action for U.S. Appl. No. 10/308,959; P&G Case 8880R; dated Feb. 16, 2006.
Advisory Action for U.S. Appl. No. 11/486,725; P&G Case 8880RC; dated Jan. 28, 2008.
Office Action for U.S. Appl. No. 11/486,725; P&G Case 8880RC; dated Jan. 28, 2009.
Office Action for U.S. Appl. No. 11/486,725; P&G Case 8880RC; dated Jan. 29, 2007.
Office Action for U.S. Appl. No. 11/486,725; P&G Case 8880RC; dated Apr. 10, 2008.
Office Action for U.S. Appl. No. 11/486,725; P&G Case 8880RC; dated Aug. 13, 2007.
Office Action for U.S. Appl. No. 11/410,808; P&G Case 9186C; dated Feb. 15, 2007.
Office Action for U.S. Appl. No. 11/410,808; P&G Case 9186C; dated Jul. 17, 2007.
Office Action for U.S. Appl. No. 11/015,111; P&G Case 9487; dated Nov. 24, 2008.
Office Action for U.S. Appl. No. 11/220,219; P&G Case 9770; dated Oct. 20, 2008.
Office Action for U.S. Appl. No. 10/367,373; dated Mar. 9, 2004.
Office Action for U.S. Appl. No. 09/425,423; P&G Case Z-3735; dated Jan. 31, 2002.
Office Action for U.S. Appl. No. 09/425,423; P&G Case Z-3735; dated Aug. 14, 2002.
Office Action for U.S. Appl. No. 10/331,799; P&G Case Z-3557; dated Apr. 19, 2005.
Office Action for U.S. Appl. No. 10/331,799; P&G Case Z-3557; dated Oct. 14, 2005.
Office Action for U.S. Appl. No. 10/331,799; P&G Case Z-3557; dated Feb. 23, 2006.
Office Action for U.S. Appl. No. 11/295,907; P&G Case 9853; dated Jun. 5, 2009.
Office Action for U.S. Appl. No. 09/993,167; P&G Case 8778; dated Dec. 18, 2002.
Office Action for U.S. Appl. No. 09/993,167; P&G Case 8778; dated Apr. 16, 2003.

* cited by examiner

ELECTRIC TOOTHBRUSHES

This application is a continuation of U.S. patent application Ser. No. 11/486,725, filed on Jul. 14, 2006, now U.S. Pat. No. 7,640,615, which is a continuation of U.S. application Ser. No. 10/308,959, now abandoned, filed Dec. 3, 2002, which claims the benefit of U.S. Provisional Application No. 60/361,625, filed Mar. 4, 2002, all of which are incorporated herein by reference.

FIELD OF THE INVENTION

The invention relates to the field of electric toothbrushes and, more particularly, the invention relates to the field of electrically powered toothbrushes having at least one bristle holder that translates or translates.

BACKGROUND OF THE INVENTION

The art is replete with techniques for transforming the rotational output of a motor or other electromotive power source into desired brushing motions. Many techniques include a shaft as a component of the drive train. The shaft may rotate, oscillate, or reciprocate. The shaft is coupled to a bristle holder. Most often, the bristle holder is driven by the shaft in a rotating or oscillating manner about an axis which is normal to the longitudinal axis of the shaft. However, there is a desire to provide bristle holders that provide a scrubbing action at the leading edge of the toothbrush head in combination with bristle holders having static bristles or other movable bristle holders.

BRIEF SUMMARY OF THE INVENTION

An electric toothbrush is provided. The electric toothbrush includes a handle having an electric motor, a head, and a neck extending between the handle and the head. The head has first end disposed adjacent to the neck and a second end opposite the first end. The head has a first bristle holder with a plurality of bristles disposed therein and a second bristle holder having a plurality of bristles disposed therein. The first bristle holder is located at the second end of said head. A rotating shaft is operatively connected to the electric motor and to the first moving bristle holder to reciprocate the first moving bristle holder in a direction transverse to a longitudinal axis of the head.

BRIEF DESCRIPTION OF THE DRAWINGS

It is believed that the present invention will be better understood from the following description taken in conjunction with the accompanying drawings in which.

DETAILED DESCRIPTION OF THE INVENTION

All patents and patent applications referenced herein are expressly incorporated herein by reference, including U.S. Provisional Application No. 60/361,625, filed Mar. 4, 2002. Reference will now be made in detail to various embodiments of the present invention, examples of which are illustrated in the accompanying drawings wherein like numerals indicate the same elements throughout the views. As will be appreciated, the present invention is directed to electric toothbrushes and electric toothbrush heads having one or more moving bristle holders. Optionally, the head might also include static bristles. The present invention can also be used with electric toothbrushes having replaceable heads. One such suitable replaceable head arrangement is disclosed in U.S. Pat. No. 5,617,601. The present invention can be used in combination with electric toothbrushes that have shafts that translate, oscillate, or reciprocate (as well as combinations thereof) to directly impart motion to each moving bristle holder. Preferably, however, the present invention is used with a shaft that rotates. Alternatively, the movable bristle holders can also be interconnected amongst themselves so that the movement of one imparts movement to another.

Figure 1:
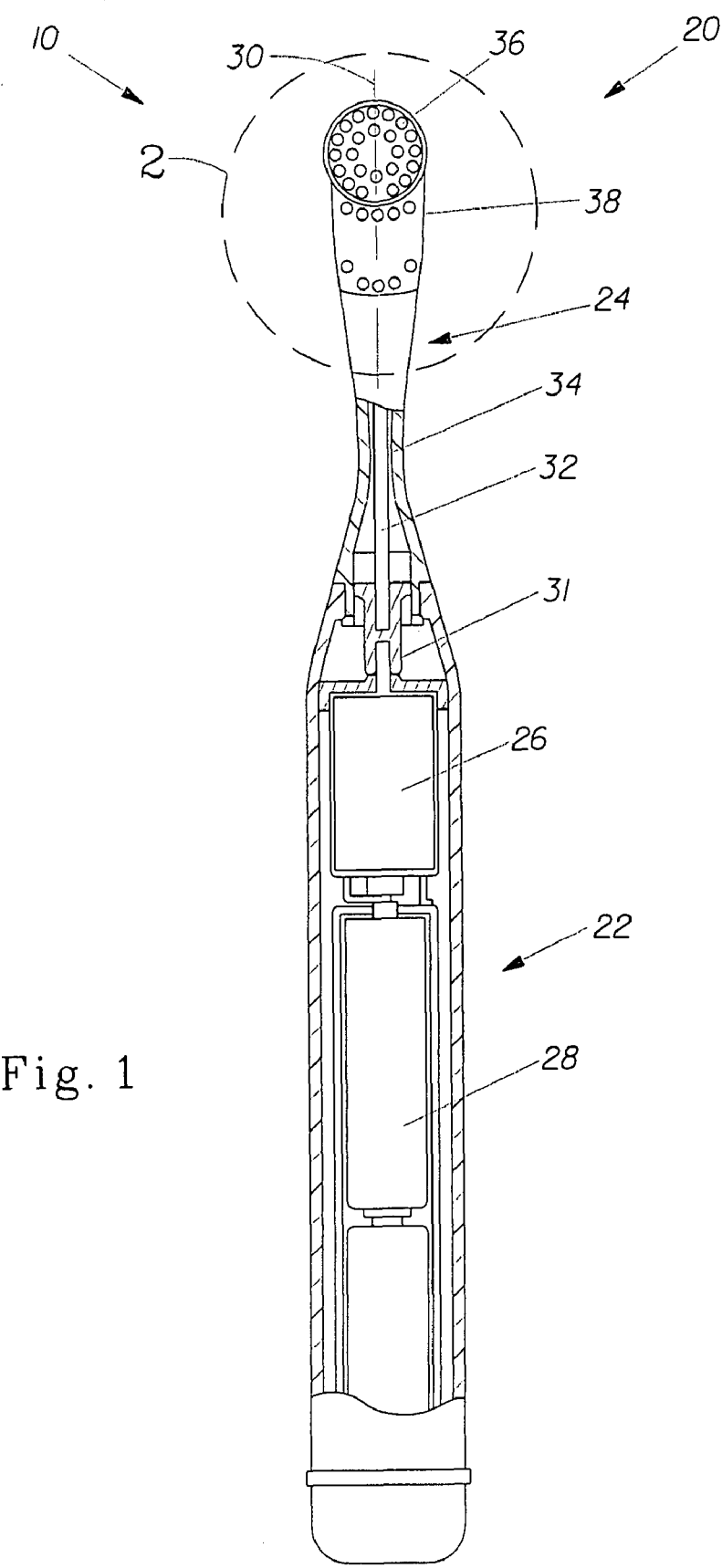
FIG. 1 is a top planar, partial sectional, top view of an electric toothbrush made in accordance with the present invention, wherein the electric toothbrush incorporates a rotating shaft.

Referring to FIG. 1, an electric toothbrush having a first bristle holder that translates or reciprocates while the second bristle holder is static relative to the head is illustrated. In other words, the shaft is not operatively connected to the second bristle holder to impart movement thereto. As used herein, the term "reciprocate" is intended to refer to a bidirectional linear motion (e.g., a back and forth motion or side to side motion). Vibration is any periodic movement having repeated cycles. Vibratory motion can have one or more frequencies and amplitudes. Vibratory motion that is substantially linear is a reciprocating motion. The electric toothbrush 10 comprises a toothbrush head portion 20, a body or handle 22, and an elongated neck 24 there between. As used herein, the term "forward" is intended to refer to the direction from the handle to the head while the term "rearward" is intended to refer to the direction from the head to the handle. In addition, the term "longitudinal" is intended to refer to a lengthwise feature of an element as seen from a top planar view thereof. For example, a longitudinal axis 30 is an axis passing through the longest dimension of an element, such as the head or a shaft. A longitudinal direction is a direction that generally corresponds to a longitudinal axis but which may not lie in the same plane as the longitudinal axis. For example, the longitudinal axes of a shaft and a toothbrush head may not lie in the same plane but generally extend in the same direction from a top planar view. Similarly, a neck and head that are angled with respect to each other may not have longitudinal axes that lie in the same plane, but do have axes that extend in the same general longitudinal direction from a top planar view. The electric toothbrushes of the present invention typically have an elongate head with a longitudinal axis passing through the longest dimension thereof. This axis typically extends in the same general direction as the longitudinal axes of the toothbrush neck and/or shaft. By the phrase "same general direction", some angular deviation is contemplated between the axes.

The handle is hollow and includes a motor 26 and batteries 28 for powering the motor. The motor 26 is operatively connected to the shaft 34 either by a coupling 31 or by a gearing assembly (not shown). A rechargeable power source can be substituted for the batteries 28. The head 20 has a longitudinal axis 30 passing there through. The longitudinal axis 30 extends in the same general longitudinal direction as a longitudinal axis 32 of shaft 34. The shaft 34 is housed at least partially within neck 24. A first bristle holder 36 is disposed at a first end of the head 20, wherein the first end is at the forward most point of the head 20. While the first bristle holder 36 is illustrated as circular in shape, other shapes and sizes can be utilized. Further, while the first bristle holder 36 is disposed at the first end of the head 20, it will be appreciated that it can be disposed away from the first end and other features, such as stationary or static bristles, might be disposed between the first bristle holder 36 and the first end of the head 20.

Figure 2:
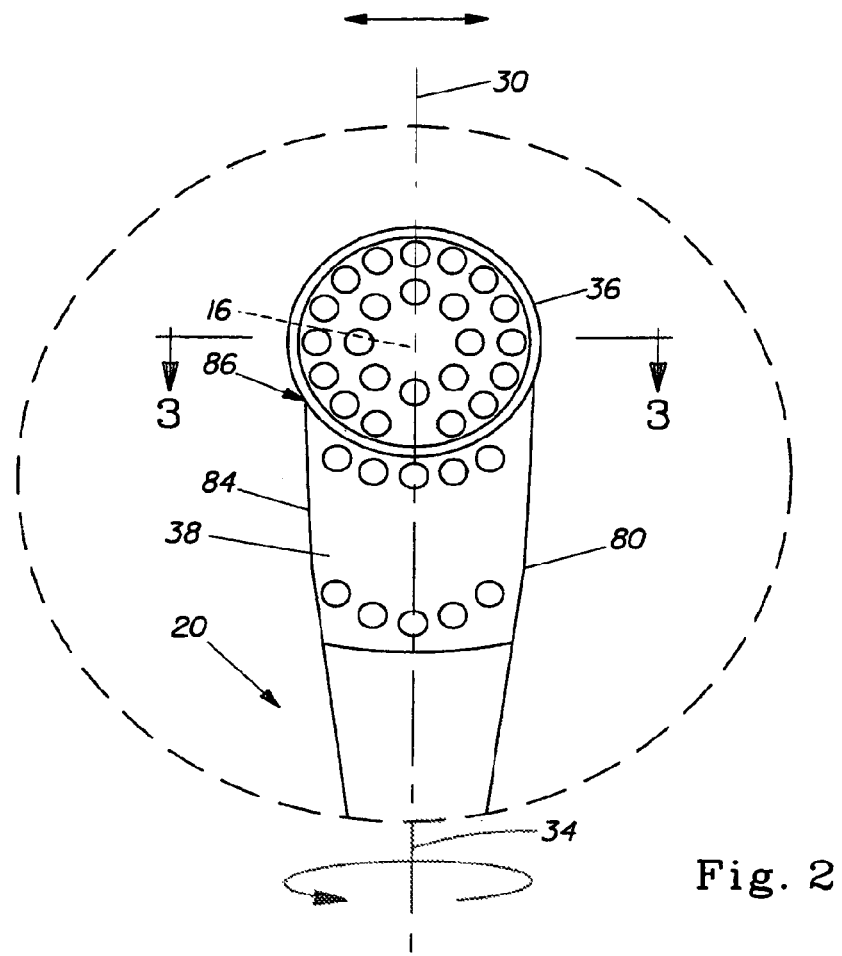
FIG. 2 is a planar, partial section top view of a toothbrush head suitable for use with the electric toothbrush of FIG. 1.
Figure 3:
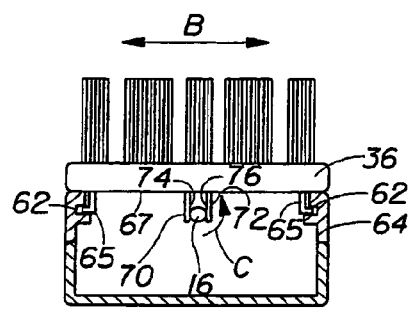
FIG. 3 is a partial sectional side view of the embodiment of FIG. 2, taken along line 3-3 thereof.

A second bristle holder 38 is disposed adjacent the first bristle holder 36. The second bristle holder 38 is static or stationary relative to the neck 24 and handle 22 or is movable as described more fully hereafter. Referring to FIGS. 2 and 3, the first bristle holder 36 is movably mounted in slots 62 in the toothbrush head 64 and driven in a reciprocating or translating, transverse motion within the slots 62 by a cam 16 included on a driving shaft 34. Alternatively, the slots 62 could be disposed in the in the first bristle holder 36 rather than the housing of the toothbrush head 64. The slots 62 guide the first bristle holder 36 in its reciprocating movement. A plurality of L-shaped fingers 65 depend from a bottom surface 67 of the first bristle holder 36 and are at least partially, slideably disposed within the slots 62. While the fingers 65 are shown as L-shaped in cross-sectional end view of FIG. 3, it is recognized that the fingers 65 can be provided in other shapes and sizes. For example, the fingers 65 might be cylindrically shaped or provided as a parallelogram.

The cam 16 can comprise an appropriately shaped bead placed over or molded and fixedly secured to the shaft 34. For example, the bead is shaped as an eccentric cam. Alternatively, the cam can include one or more rectilinear, curvilinear or other kind of bend, as shown by way of example in the embodiment of FIG. 7A. First 70 and second 72 cam followers also depend from the bottom surface 67 of the first bristle holder 36. The cam followers are, for example, offset from the longitudinal axis 30 of the first bristle holder 36 (i.e., are not symmetrically disposed about the longitudinal axis 30 of the first bristle holder) and straddle or capture the cam 16. While the cam followers 70 and 72 are preferably offset from the longitudinal axis of the first bristle holder 36, the cam followers 70 and 72 are preferably disposed at about the middle of the first bristle holder 36. In other words, the cam followers are disposed about mid-way between the forward-most end of the first bristle holder 36 and the rearward-most end of the first bristle holder 36, although depending upon the location of the slots 62, the location of the cam followers might vary from about the middle of the first bristle holder 36. As the motor 26 rotates the shaft 34 in accordance with arrow C, the cam 16 comes into contact with a surface 74 of the first cam follower 70 and drives the first cam follower 70, and therefore, the first bristle holder 36 away from a first side 80 of the head portion 20 along a transverse axis 82 of the first bristle holder 36. As the shaft 34 continues to rotate, the cam 16 becomes disengaged from the first cam follower 70. The cam 16 then comes into contact with a surface 76 of the second cam follower 72 and drives the second cam follower 72, and therefore, the first bristle holder 36 toward the second side 84 of the head portion 20. A clearance 86 is provided between the first and second bristle holders 36, 38 to accommodate the spacing requirements of this motion. As this back and forth or side to side motion is repeated (as the shaft 34 continues to rotate), a sweeping motion is provided that provides enhanced cleaning action to the teeth in the direction of arrow B in FIG. 3.

Figure 4:
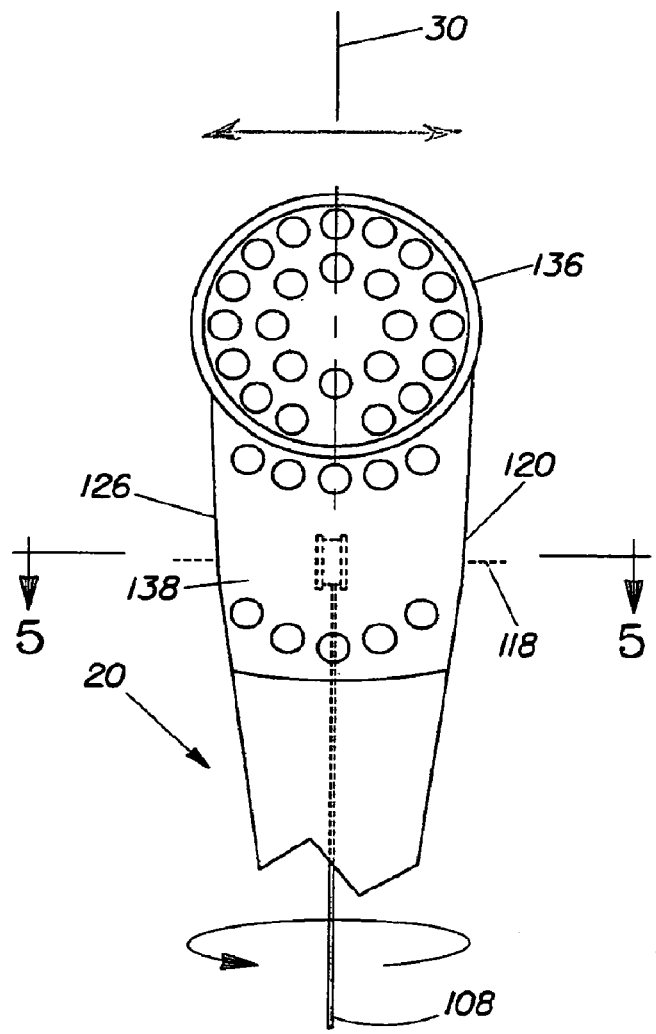
FIG. 4 is a planar, partial sectional top view of a second embodiment of a toothbrush head suitable for use with the electric toothbrush of FIG. 1.
Figure 5:
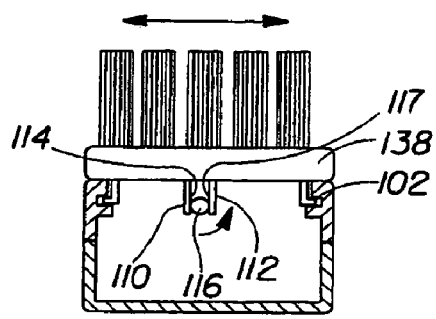
FIG. 5 is a partial sectional side view of the embodiment of FIG. 4, taken along line 5-5 thereof.

Referring to FIG. 4 and FIG. 5, in a second embodiment of the electric toothbrush, the second bristle holder 138 is movably mounted in slots 102 in the toothbrush head 20 and separately driven in a reciprocating or translating, transverse motion within the slots 102 by a cam 116 included on a driving shaft 108, in a similar manner to the cam 16 shown in FIGS. 2 and 3. The first bristle holder 136 is stationary. The cam 116 can comprise an appropriately shaped bead placed over or molded and fixedly secured to the shaft 108 as in the first embodiment. First 110 and second 112 cam followers depend from a bottom surface of the second bristle holder 138. The cam followers are, for example, offset from the longitudinal axis 30 of the second bristle holder and straddle or capture the cam 116. As the motor 26 (see FIG. 1) rotates the shaft 108, the cam 116 comes into contact with a surface 114 of the first cam follower 110 and drives the first cam follower 110, and therefore, the second bristle holder 138 away from a first side 120 of the brush portion 20 along a transverse axis 118 of the head. As the shaft 108 continues to rotate, the cam 116 becomes disengaged with the first cam follower 110. The cam 116 then comes into contact with a surface 117 of the second cam follower 112 and drives the second cam follower 112, and therefore, the second bristle holder 138 toward the second side 126 of the head. As this back and forth or side to side motion is repeated (as the shaft 108 continues to rotate), the desired sweeping motion is provided.

Figure 6:
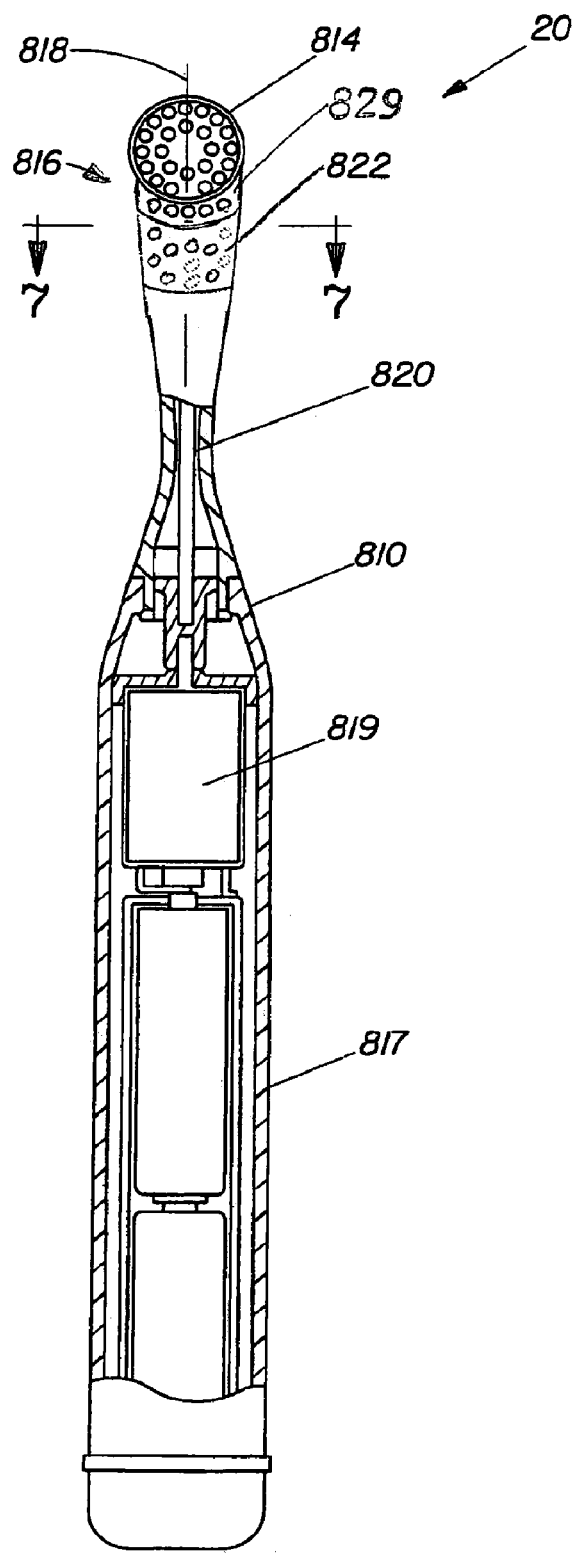
FIG. 6 is a bottom view of an toothbrush having a second bristle holder. The toothbrush is shown in partial section.

Referring to FIGS. 6 to 17, various embodiments incorporating a second movable bristle holder will now be described in combination with a first movable bristle holder similar to the first bristle holder 36 previously described with respect to FIGS. 3 and 4. A first bristle holder 814 of the head 816 has a pair of cam followers 815 (see, e.g., FIG. 7A) that depend from a bottom surface of the first bristle holder and that operatively engage the shaft 820 to reciprocate the first bristle holder 814 in a side to side motion substantially transverse to the longitudinal axis 818 of the head 816, as previously discussed. The electric toothbrush 810 has a head 816 and a body or handle 817. The electric toothbrush 810 includes a motor 819 and batteries for powering the motor. The head portion 816 has a longitudinal axis 818. The first bristle holder 814 is illustrated as circular. However, other shape bristle holders are contemplated and within the scope of the invention. The motor 819 is operative to rotate the shaft 820. In short, with regard to the construction and operation of the shaft 820 in relation to the first bristle holder 814, the electric toothbrush 810 is similar to the toothbrush described in reference to FIGS. 1 to 3. However, the electric toothbrush 810 also has a second bristle holder disposed adjacent the first bristle holder, such as second bristle holder 822. While it is desirable to locate the second bristle holder directly adjacent the first bristle holder, it is contemplated that a gap may be provided between the first and second bristle holders. In addition, the space between the first and second bristle holders might be filled with static, stationary or fixed bristles that are embedded in fixed or stationary third bristle holder, as shown in FIG. 6, which forms part of the toothbrush head. In electric toothbrush 810, the second bristle holder is movable and separately associated with, and separately driven by, the drive shaft 820, and static bristles 829 are positioned between the first and second bristle holders 814, 822.

Figure 7:
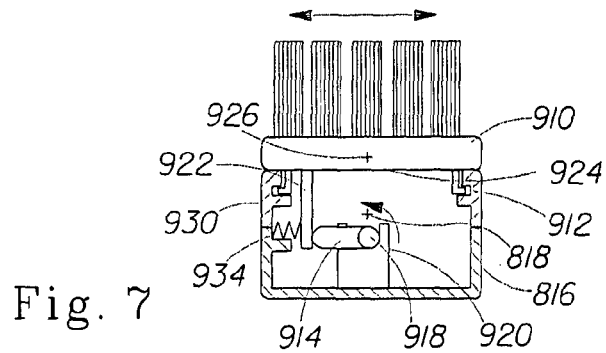
FIG. 7 is a sectional view taken along line A-A in FIG. 6 of a first embodiment of a toothbrush head.
Figure 7A:
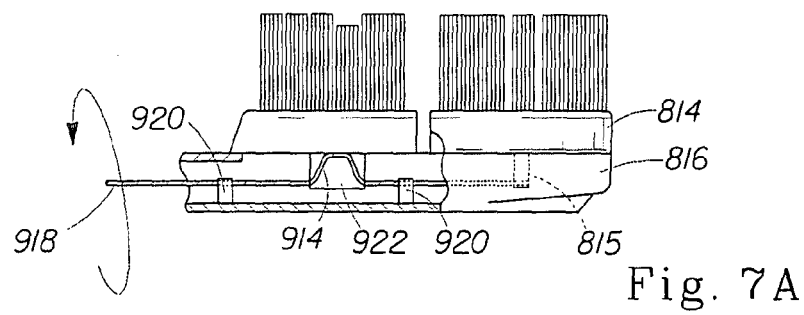
FIG. 7A is a partial sectional side view of the head of FIG. 7, taken along line B-B of FIG. 6.

For example, referring to FIG. 7, a second bristle holder 910 is movably mounted in slots 912 in the toothbrush head 816 and separately driven in a vibratory, side-to-side, motion in a direction substantially transverse to the direction of the longitudinal axis 818 by an eccentric cam 914 included on a driving shaft 918. The cam 914 and other cams described below can comprise one or more bends in the shaft 918, as shown for example in FIG. 7A, and as seen in views of other embodiments described below in FIG. 11, FIG. 12, and FIG. 13. Alternatively, the cam 914 can be provided as a separate piece, which is attached to the shaft 918 by adhesive, a press or snap fit, a co-molding or any other mechanical or chemical means known in the art. Optionally, the driving shaft is supported by a shaft support 920. A cam follower 922 depends from a bottom surface 924 of the second bristle holder 910. The cam follower 922 is offset from a longitudinal axis 926 of the second bristle holder. As the motor 819 of the toothbrush 810 rotates the shaft 918, the cam 914 comes into contact with a cam contact surface 928 of the cam follower 922 and drives the cam follower 922, and therefore, the second bristle 910 holder toward one side 930 of the toothbrush 810 and away from the longitudinal axis 818 of the head portion 816. As the shaft 918 continues to rotate, the cam 914 becomes disengaged with the cam follower 922. A resilient biasing member such as a spring 934, lodged between a wall of the head portion 816 and a second surface of the cam follower, urges the cam follower 922, and therefore the second bristle holder 910, back toward the longitudinal axis 818 of the head portion 816. As this back and forth or sided to side motion is repeated (as the shaft 918 continues to rotate), a sweeping or brushing motion is provided that is distinct from and complimentary to the motion provided by the first bristle holder 814. The stroke and/or frequency of the second bristle holder 910 can be changed by varying the construction of the spring and placement and/or sizing of the cam 914 and the cam follower 922. For example, the cam follower 922 might be placed closer to the axis 926 to provide a shorter stroke or the cam follower 922 or a stronger spring might be provided to increase the rate of return of the second bristle holder 910 or more than one spring might be provided. Alternatively, the cam follower 922 might form an acute angle with the bottom surface 924 of the second bristle holder 910 or the first surface can be provided as accurate, curvilinear, or in other complex forms as opposed to the planar surface shown in FIG. 7.

Figure 8:
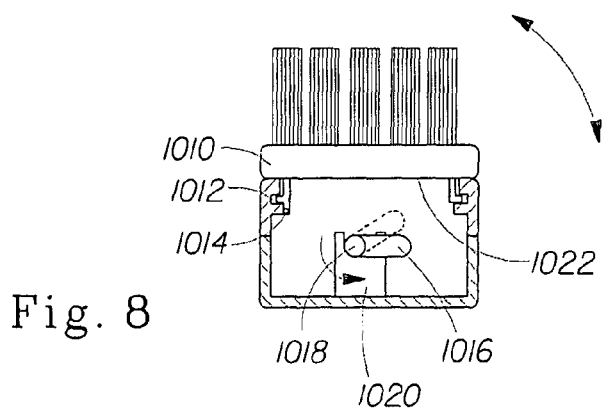
FIG. 8 is a sectional view taken along A-A in FIG. 6 of a second embodiment of a toothbrush head.

Referring to FIG. 8, in a second embodiment of the electric toothbrush 810, a second bristle holder 1010 is movably mounted in slots 1012 in the toothbrush head 816 and separately driven in a vibratory, swinging or pivoting motion about a hinge or pivot 1014, by a cam 1016 included on a driving shaft 1018. The cam 1016 can comprise one or more bends in the shaft 1018 or be provided as a separate piece as previously discussed. Optionally, the driving shaft is supported by a shaft support 1020. A cam contact surface 1022 is located on a bottom surface of the second bristle holder 1010. As the motor 819 of the toothbrush 810 rotates the shaft 1018, the cam 1016 comes into contact with the cam contact surface 1022 and drives or pushes the second bristle holder 1010 causing the second bristle holder to swing or pivot about the hinge or pivot 1014. As the shaft 1018 continues to rotate, the cam 1016 becomes disengaged with the cam contact surface 1022. During use, as the cam 1016 comes in contact with the cam contact surface 1022, bristles of the second bristle holder 1010 are urged against the users teeth with greater force. Preferably, bristles of the second bristle holder 1010 are urged between the teeth of the user to provide a cleaning and flossing function. As the cam disengages with the contact surface 1022, bristles pressing against the teeth of the user urge the second bristle holder away from the users teeth. As this swinging or pivoting motion is repeated (as the shaft 1018 continues to rotate), a flossing or deep cleaning motion is provided that is distinct from and complimentary to the motion provided by the first bristle holder 814.

Figure 9:
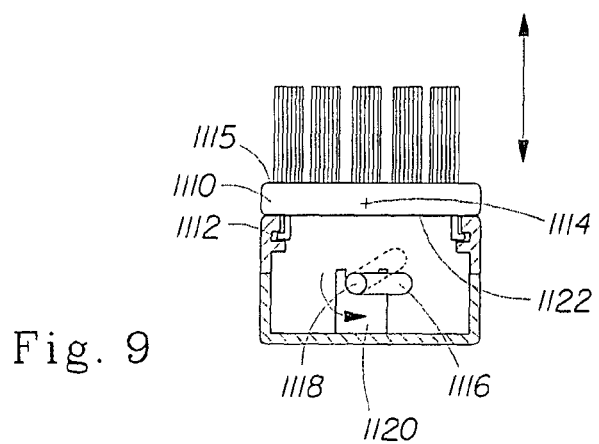
FIG. 9 is a sectional view taken along A-A in FIG. 6 of a third embodiment of a toothbrush head.

Referring to FIG. 9, in a third embodiment, a second bristle holder 1110 is movably mounted in slots 1112 in the toothbrush head 816 and separately driven in a vibratory, lifting or vertical pulsating motion (e.g., in a direction substantially perpendicular to the longitudinal axis 1114 and substantially parallel to a surface 1115 of the second bristle holder 1110 as shown by way of example in FIG. 9) within the slots 1112, by a cam 1116 included on a driving shaft 1118. Optionally, the driving shaft is supported by a shaft support 1120. The cam 1116 can comprise one or more bends in the shaft 1118 or can be provided as a separate piece as previously discussed. A cam contact surface 1122 is located on a bottom surface of the second bristle holder 1110. As the motor 819 (see FIG. 6) of the toothbrush 810 rotates the shaft 1118, the cam 1116 comes into contact with the cam contact surface 1122 and drives or lifts in a vibratory, lifting, or vertical pulsating motion the second bristle holder 1110 causing the second bristle holder to lift or pulsate in a direction away from the head portion 816 and toward the teeth of a toothbrush user (not shown). As the shaft 1118 continues to rotate, the cam 1116 becomes disengaged with the cam contact surface 1122. During use, as the cam 1116 comes in contact with the cam contact surface 1122, bristles of the second bristle holder 1110 are urged against the user's teeth with varying degrees of force. Preferably, bristles of the second bristle holder 1110 are urged between the teeth of the user to provide a cleaning and flossing function. As the cam disengages with the contact surface 1122, bristles pressing against the teeth of the user urge the second bristle holder away from the user's teeth and back toward the head portion 816. As this lifting or vertical pulsating motion is repeated (as the shaft 1118 continues to rotate), a flossing or deep cleaning motion is provided that is distinct from and complimentary to the motion provided by the first bristle holder 814.

Figure 10:
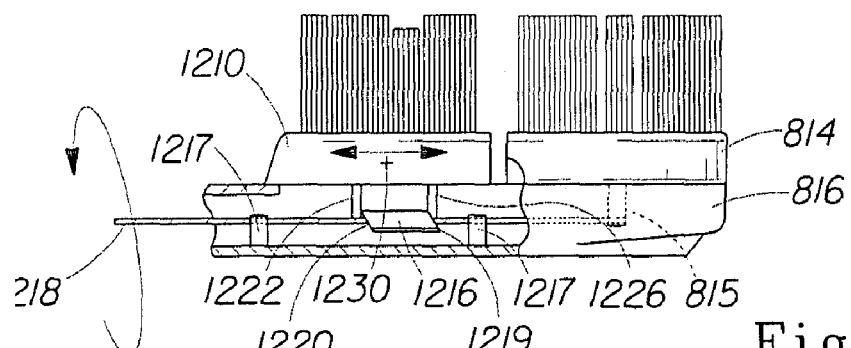
FIG. 10 is a partial sectional view taken along B-B in FIG. 6 of a fourth embodiment of a toothbrush head.

Referring to FIG. 10, in a fourth embodiment, a second bristle holder 1210 is movably mounted in slots (not shown, but similar to the slots 912 illustrated in FIG. 7) in the toothbrush head 816 and separately driven in a reciprocating or translating, longitudinal motion within the slots by a cam 1216 included on a driving shaft 1218. Optionally, the shaft is supported by shaft supports 1217. The shaft supports may include C or U shaped portions (not shown) that are operative to receive and snap around the shaft. Other means for retaining a shaft in a support are known in the art. The cam 1216 can comprise a shaped bead, with an appropriate eccentric configuration, placed or molded over and firmly secured to the shaft 1218. In one embodiment, the cam 1216 includes a pair of acutely angled surfaces 1219, 1220 which are inclined in the same direction and at the same angle of inclination, but which are disposed at opposite ends of the cam 1216. The direction of inclination and angle of inclination can be varied as desired to change the frequency and stroke of the second bristle holder 1210. First 1222 and second 1226 cam followers depend from a bottom surface of the second bristle holder 1210. The cam followers 1222, 1226 are offset or spaced from a transverse axis 1230 of the second bristle holder. The cam followers 1222, 1226 straddle and/or capture the cam 1216 so that the angled surfaces 1219, 1220 slidably engage the free ends of the cam followers 1222 and 1226. As the motor 819 (see FIG. 6) of the toothbrush 810 rotates the shaft 1218, the first acutely angled surface 1220 of the cam 1216 comes into contact with a surface of the first cam follower 1222 and drives the cam follower, and therefore, the second bristle holder 1210, away from the first bristle holder 814 along the longitudinal axis 818 of the head portion 816. As the shaft 1218 continues to rotate, the cam 1216 becomes disengaged with the first cam follower 1222. The second acutely angled second surface 1219 of the cam 1216 then comes into contact with a surface of the second cam follower 1226 and drives the second cam follower 1226, and therefore, the second bristle holder 1210, back toward the first bristle holder 814. As this back and forth motion is repeated (as the shaft 1218 continues to rotate), a scrubbing action is provided by the reciprocating or translating motion that is distinct from and complimentary to the motion provided by the first bristle holder 814.

Figure 11:
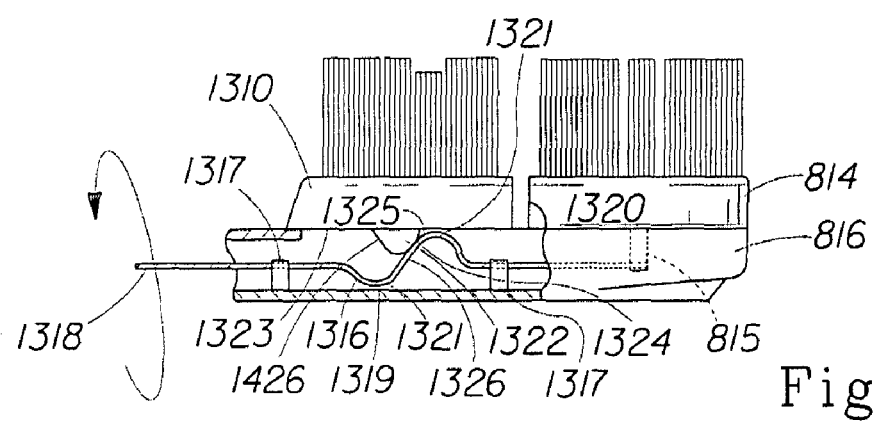
FIG. 11 is a partial sectional view taken along B-B in FIG. 6 of a fifth embodiment a toothbrush head.
Figure 12:
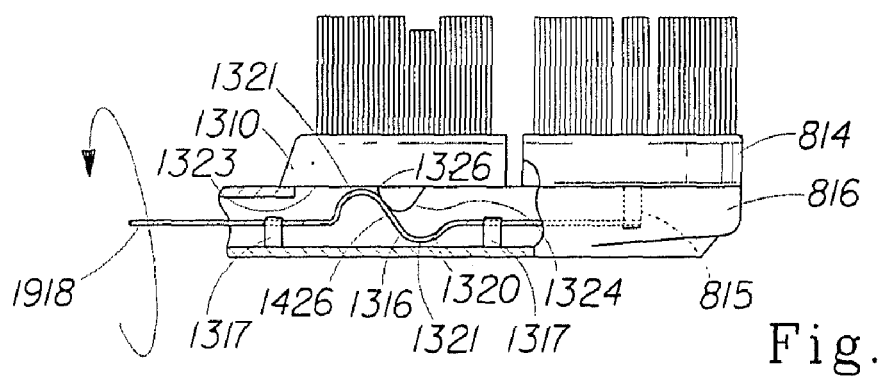
FIG. 12 is a partial sectional view of the fifth embodiment of FIG. 11. The shaft is shown rotated to a different position than shown in FIG. 12.

Referring to FIG. 11 and FIG. 12, in a fifth embodiment of the electric toothbrush 810, a second bristle holder 1310 is movably mounted in slots (not shown, but similar to the slots 912 illustrated in FIG. 7) in the toothbrush head 816 and separately driven in an reciprocating or translating, longitudinal motion, by a cam 1316 included on a driving shaft 1318. Optionally, the shaft is supported by shaft supports 1317. The shaft supports may include C or U shaped portions (not shown) that are operative to receive and snap around the shaft. Other means for retaining a shaft in a support are known in the art. The cam 1316 is sinusoidal or curvilinear in nature in that it has one or more adjacent arcuate bends 1319 and 1320 in the shaft 1318. The arcuate bends 1319, 1320 each have an apex 1321, and the apexes 1321 are disposed on opposite sides of the driving shaft 1318. A cam follower 1322 depends from a bottom surface 1323 of the second bristle holder 1310 and is disposed between the apexes 1321 of the cam 1316. As the motor 819 of the toothbrush 810 rotates the shaft 1318, a first surface 1325 of the cam 1316 comes into contact with a first surface 1324 of the cam follower 1322 and drives the cam follower 1322, and therefore, the second bristle holder 1310 away from the first bristle holder 814 in a direction along the longitudinal axis 818 of the head portion 816. As the shaft 1318 continues to rotate, the first surface 1325 of the cam 1316 reaches the apex 1321 and becomes disengaged with the first cam follower surface 1324. A second surface 1326 of the cam 1316 then comes into contact with a second surface 1426 of the cam follower 1322 and drives the cam follower 1322, and therefore, the second bristle holder 1310 back toward the first bristle holder 814. As this back and forth motion is repeated (as the shaft 1318 continues to rotate), a scrubbing action is provided by the reciprocating or translating motion that is distinct from and complimentary to the motion provided by the first bristle holder 814. The stroke and frequency of the reciprocating or translating motion can be varied by changing the spacing between the apexes and/or the amplitude or height of the apexes.

Figure 13:
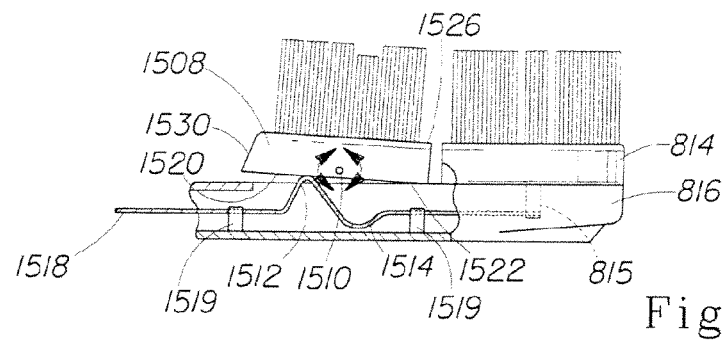
FIG. 13 is a partial sectional view taken along B-B in FIG. 6 of a sixth embodiment of a toothbrush head.

Referring to FIG. 13, in a sixth embodiment of the electric toothbrush 810, a second bristle holder 1508 is movably mounted to the toothbrush head 816 with a pivot 1510, which can be provided in the form of a pin or hinge, is installed at a centrally located transverse axis of the second bristle holder 1508. In one embodiment, the second bristle holder 1508 pivots about a pin, which is anchored in the sidewalls of the toothbrush neck or head 816 at the midpoint of the second bristle holder 1508. The second bristle holder 1508 is separately driven in a vibratory, swinging, teetering or rocking motion by a cam comprised of first 1512 and second 1514 cam portions included on a driving shaft 1518. Optionally, the shaft is supported by shaft supports 1519. The shaft supports may include C or U shaped portions (not shown) that are operative to receive and snap around the shaft. Other means for retaining a shaft in a support are known in the art. The cam portions 1512, 1514 can comprise one or more rectilinear, curvilinear or other bends in the shaft 1518. As is illustrated in FIG. 13 the first cam portion 1512 is located adjacent a first side of the pivot and the second cam portion 1514 is located adjacent a second side of the pivot. The second cam portion 1514 can comprise a portion of the remote-most end of the shaft 1518. First 1520 and second 1522 cam contact surfaces are located on a bottom surface of the second bristle holder 1508. As is the case with all the described embodiments, the amplitude or height of the bends or eccentricities that make up the first and second cam portions 1512, 1514 are large enough reach the related cam contact surface(s) and to drive the second bristle holder a desired distance toward, into, across or along a toothbrush users teeth. As the motor 819 of the toothbrush 810 rotates the shaft 1518, the first cam portion 1512 comes into contact with the first cam contact surface 1520 and drives or lifts (relative to the figure) a first end 1530 of the second bristle holder 1508 causing the first end 1530 to rock or move about the pivot 1510 in a direction away from the head portion 816 and toward the teeth of a toothbrush user (not shown). This action lowers a second end 1526 of the second bristle holder back toward the head portion 816. As the shaft 1518 continues to rotate, the first cam portion 1512 becomes disengaged with the first cam contact surface 1520 and the second cam portion 1514 engages the second cam contact surface 1522. The second cam portion 1514 drives or lifts (relative to the figure) the second end 1526 of the second bristle holder 1508 causing the second end 1522 to rock or move about the pivot 1510 in a direction away from the head portion 816 and toward the teeth of the toothbrush user. This action lowers a first end 1530 of the second bristle holder back toward the head portion 816. During use, as the first and second cam portions 1512, 1514 alternately come in contact with the first and second cam contact surfaces 1520, 1522, bristles of the second bristle holder 1508 are urged against teeth of the user with varying degrees of force. Preferably, bristles of the second bristle holder 1508 are urged between the teeth of the user to provide a cleaning and flossing function. As the rocking or pivoting motion is repeated (as the shaft 1518 continues to rotate), a flossing or deep cleaning motion is provided that is distinct and complimentary to the motion provided by the first bristle holder 814.

Figure 14:
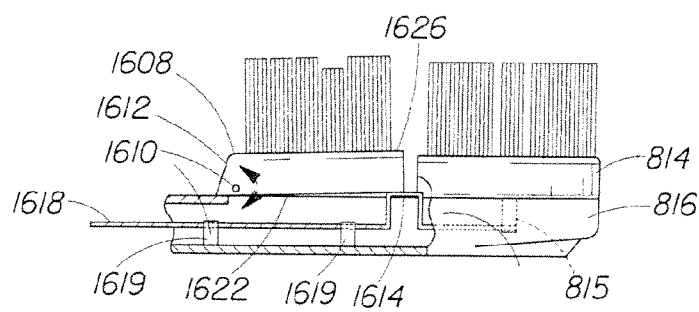
FIG. 14 is a partial sectional view taken along B-B in FIG. 6 of a seventh embodiment of a toothbrush head.

Referring to FIG. 14, in a seventh embodiment of the electric toothbrush 810, a second bristle holder 1608 is movably mounted to the toothbrush head 816 with a pivot 1610, which can be provided in the form of a pin or of a hinge, installed at a transverse axis of the second bristle holder 1608.

In one embodiment, the second bristle holder 1608 pivots about a pin, which is anchored in the side walls of the toothbrush neck at one end of the second bristle holder 1608. The transverse axis is, for example, adjacent to a first end 1612 of the second bristle holder 1608. The second bristle holder 1608 is separately driven in a vibratory, swinging, pivoting or rocking motion by a cam 1614 included on a driving shaft 1618. Optionally, the shaft is supported by shaft supports 1619. The shaft supports may include C or U shaped portions (not shown) that are operative to receive and snap around the shaft. Other means for retaining a shaft in a support are known in the art. The cam 1614 can comprise one or more bends in the shaft 1618. For example, the bends can be rectilinear, curvilinear or other kinds of bends. A cam contact surface 1622 is located on a bottom surface of the second bristle holder 1608 adjacent to a second end 1626 thereof. As the motor 819 of the toothbrush 810 rotates the shaft 1618, the cam 1614 comes into contact with the cam contact surface 1622 and drives or lifts (relative to the figure) the second end 1626 of the second bristle holder 1608 causing the second end 1626 of the second bristle holder 1608 to rock or move about the pivot 1610 in a direction away from the head portion 816 and toward the teeth of a toothbrush user (not shown). As the shaft 1618 continues to rotate, the cam 1614 becomes disengaged with the cam contact surface 1622. During use, as the cam 1614 comes in contact with the cam contact surface 1622, bristles of the second bristle holder 1608 are urged against teeth of the user with a varying degree of force. Preferably, bristles of the second bristle holder 1608 are urged between the teeth of the user to provide a cleaning and flossing function. As the cam disengages with the contact surface 1622, bristles pressing against the teeth of the user urge the second bristle holder away from the users teeth and back toward the head portion 816. As this swinging or pivoting motion is repeated (as the shaft 1618 continues to rotate), a flossing or deep cleaning motion is provided that is distinct from, and complimentary to, the motion provided by the first bristle holder 814.

Figure 15:
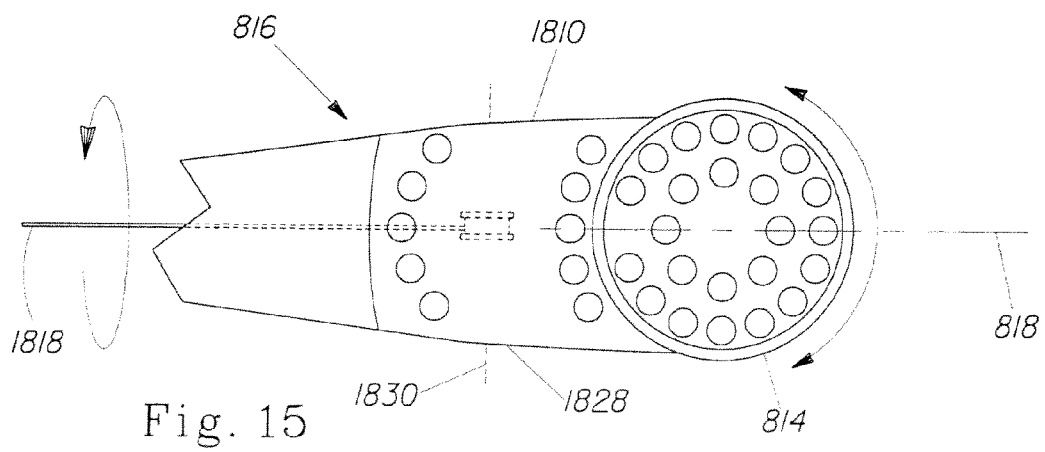
FIG. 15 is a bottom view of a head portion of a eighth embodiment of a toothbrush head.
Figure 16:
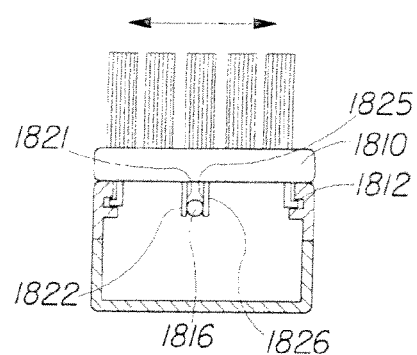
FIG. 16 is a partial sectional view of the eighth embodiment of a toothbrush head of FIG. 15.

Referring to FIG. 15 and FIG. 16, in an eighth embodiment of the electric toothbrush 810, a second bristle holder 1810 is movably mounted in slots 1812 in the toothbrush head 816 and separately driven in a reciprocating or translating, transverse motion within the slots 1812 by a cam 1816 included on a driving shaft 1818. This motion is the same type of motion previously described with respect to the second bristle holder 910 shown in FIG. 7 and is also the same type of motion that the first bristle holder 814 undergoes. The cam 1816 can comprise an appropriately shaped bead placed over or molded and fixedly secured to the shaft 1818. The transverse motion of the second bristle holder 1810 can be out of phase with the transverse movement of the first bristle holder 814. For example, as the first bristle holder 814 travels toward one side of the head 816, the second bristle holder 1810 would be traveling toward the opposite side of the head 816. The cam can include one or more rectilinear, curvilinear or other kind of bend. First 1822 and second 1826 cam followers depend from a bottom surface of the second bristle holder 1810. The cam followers are, for example, offset from the longitudinal axis 818 of the second bristle holder and straddle or capture the cam 1816. As the motor 819 (see FIG. 6) rotates the shaft 1818, the cam 1816 comes into contact with a surface 1821 of the first cam follower 1822 and drives the first cam follower 1822, and therefore, the second bristle holder 1810 away from a first side 1828 of the head portion 816 along an axis 1830 transverse to the longitudinal axis 818 of the head portion 816. As the shaft 1818 continues to rotate, the cam 1816 becomes disengaged with the first cam follower 1822. The cam 1816 then comes into contact with a surface 1825 of the second cam follower 1826 and drives the second cam follower 1826, and therefore, the second bristle holder 1810 back toward the first side 1828 of the head portion 816. As this back and forth or side to side motion is repeated (as the shaft 1818 continues to rotate), a sweeping motion is provided that is distinct from and complimentary to the motion provided by the first bristle holder 814.

Figure 17:
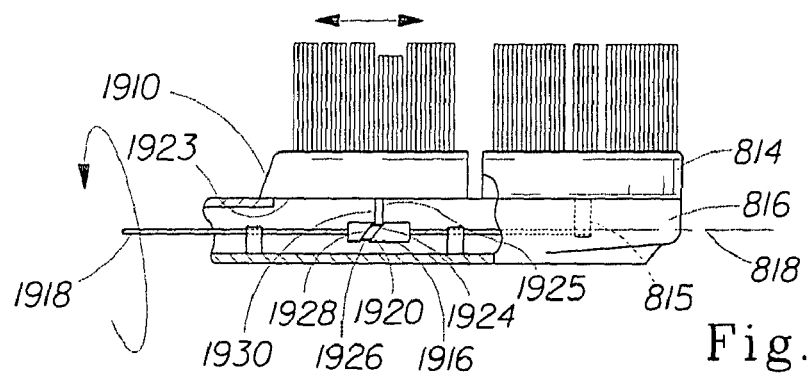
FIG. 17 is a partial sectional view taken along B-B in FIG. 6 of a ninth embodiment of a toothbrush head.

Referring to FIG. 17, in a ninth embodiment of the electric toothbrush 810, a second bristle holder 1910 is movably mounted in slots (not shown) in the toothbrush head 816 and separately driven in an reciprocating or translating, longitudinal motion, by a cam 1916 included on a driving shaft 1918. The cam 1916 can comprise a shaped bead, with an appropriate configuration, placed or molded over and firmly secured to the shaft 1918. The cam 1916 includes a reversing spiral or helical groove 1920. The spiral or helical groove extends around a circumference of the bead and spirals about a longitudinal axis of the bead. For example, the longitudinal axis coincides with the shaft 1918. A cam follower 1922 depends from a bottom surface 1923 of the second bristle holder 1910. The cam follower 1922 is slidingly received within the spiral groove 1920. As the motor 819 of the toothbrush 810 rotates the shaft 1918, a first surface 1924 of the spiral groove 1920 comes into contact with a first surface 1925 of the cam follower 1922 and drives the cam follower 1922, and therefore, the second bristle holder 1910 away from the first bristle holder 814 along the longitudinal axis 818 of the head portion 816. As the shaft 1918 continues to rotate, the cam follower 1922 reaches an apex 1926 of the spiral groove 1920 and the first surface 1924 of the spiral groove 1920 becomes disengaged with the first cam surface 1925. A second surface 1928 of the spiral groove 1920 then comes into contact with a second surface 1930 of the cam follower 1922 and drives the cam follower 1922, and therefore, the second bristle holder 1910 back toward the first bristle holder 814. As this back and forth motion is repeated (as the shaft 1918 continues to rotate), a scrubbing motion is provided that is distinct and complimentary to the motion provided by the first bristle holder 814. Optionally cam 1916 is eccentrically mounted on the shaft 1918 and the longitudinal axis of the bead or cam 1916 does not coincide with the shaft 1918. In this case, if the cam follower 1922 is made long enough to ride on the bottom of the spiral groove 1920, a lifting or vertical pulsing force is provided to the second bristle holder as the eccentrically mounted came is rotated by the shaft. Alternately, or additionally, the depth of the groove is varied. The variation in depth provides lifting or vertical pulsing forces to the cam follower and therefore to the second bristle holder. The spiral groove may be replaced with a groove that cycles back and forth along the longitudinal axis of the bead several times as it circles the bead. This sort of groove can be used to increase the reciprocating frequency of the second bristle holder.

Figure 18:
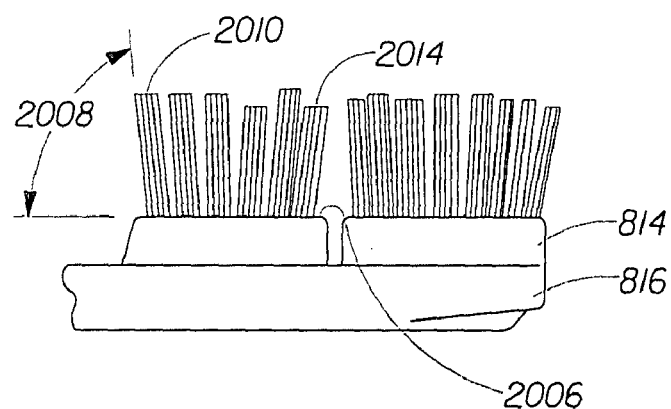
FIG. 18 is a side view of a toothbrush showing a first exemplary alternate bristle arrangement.
Figure 19:
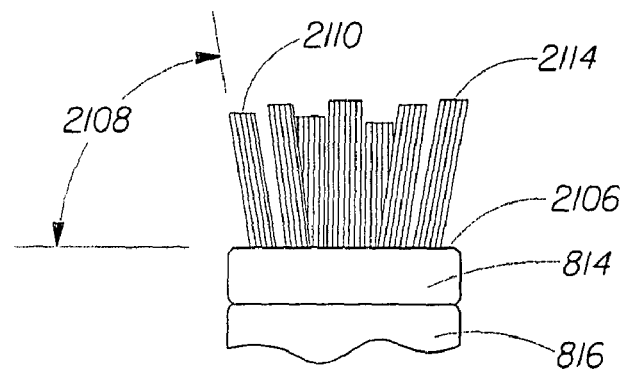
FIG. 19 is an end view taken along D-D of FIG. 8 showing a second exemplary bristle arrangement.

While the above-described embodiments of the present invention have been illustrated for simplicity with bristles which extend in a direction substantially perpendicular to the longitudinal axis 818 and the surface (for example see 1115 of FIG. 9) of the bristle holders, it is contemplated that the bristles might be arranged differently to complement or further enhance the motions of the first and/or second bristle holders. Referring to FIG. 18, some or all of the bristles might extend in a direction which forms an acute angle 2008 to a surface 2006 of the bristle holder and extends in a direction toward or away from the handle, such as shown by way of example in FIG. 18 with respect to bristles 2010 and 2014 respectively. Referring to FIG. 19, in another embodiment, some of the bristles might extend outwardly away from head, in another direction, again forming an acute angle 2108 with respect to the surface of the bristle holder, as shown by way in FIG. 19 with respect to bristles 2110 and 2114. Elastomeric bristles or bristles of varying height might also be used, such as described in U.S. Pat. Nos. Des. 330,286 and Des. 434,563. Other preferred bristle arrangements suitable for use include those arrangements described in whole or part in U.S. Pat. Nos. 6,006,394; 4,081,876; 5,046,213; 5,335,389; 5,392,483; 5,446,940; 4,894,880; and international publication no. WO 99/23910.

The invention has been described with reference to particular embodiments. Modifications and alterations will occur to others upon reading and understanding this specification. For example, while the second bristle holders of the embodiments illustrated in FIGS. 6 to 17 have been described as driven directly by the shaft, it is contemplated that second bristle holder could be directly driven by the first bristle holder by a link, pin, gearing, rack and pinion, or other mechanical connection between the first bristle holder and the second bristle holder. Further, while the first bristle holder has been illustrated as cylindrical in shape, the first bristle holder can encompass alternative shapes and sizes. It is intended that these and other modifications and alterations are included insofar as they come within the scope of the appended claims or equivalents thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A replaceable head for an electric toothbrush, the replaceable head having a first end and a second end, the replaceable head further comprising:
   a neck adapted to engage an electric toothbrush handle, wherein the first end is disposed adjacent to the neck and the second end is disposed opposite to the first end;
   a first bristle holder having a plurality of bristles disposed therein;
   a second bristle holder having a plurality of bristles disposed therein, wherein the first bristle holder is located at the second end of the head and the second bristle holder is located at the first end of the head, and wherein the tips of the bristles of the first and second bristle holders are capable of moving in a side-to-side direction generally transverse to both a longitudinal axis of the head and a general orientation of the bristles in response to a rotational movement of a shaft; and
   wherein at least one of said first bristle holder and said second bristle holder includes an upper surface and a lower surface with the bristles thereon extending from the upper surface, the lower surface including a pair of cam followers that depend from middle portion thereof and operatively engage a cam on the shaft the lower surface further including a pair of depending fingers disposed on opposite sides of the cam followers, the depending fingers being engaged within guide slots formed in opposite sides of the head.

2. The replaceable head of claim 1, wherein the cam followers are offset from a longitudinal axis of the shaft.

3. The replaceable head of claim 1, wherein the other of the first bristle holder and the second bristle holder has a cam follower depending from a lower surface and a resilient biasing member lodged against the cam follower.

4. The replaceable head of claim 3, wherein the cam follower engages the cam shaft.

5. The replaceable head of claim 3, wherein the cam follower is offset from a longitudinal axis of the shaft.

6. The replaceable head of claim 3, wherein the resilient member comprises a spring.

7. The replaceable head of claim 1, wherein the first bristle holder and the second bristle holder are positioned consecutively along the longitudinal axis of the head.

8. The replaceable head of claim 1, Thither comprising static bristles disposed between the first bristle holder and the second bristle holder.

\* \* \* \* \*